United States Patent [19]

Coey et al.

[11] Patent Number: 4,838,706
[45] Date of Patent: Jun. 13, 1989

[54] THERMAL ANALYSIS

[75] Inventors: John M. D. Coey; Dominic H. Ryan, both of Dublin, Ireland

[73] Assignee: The Provost, Fellows and Scholars of the College of the Holy and Undivided Trinity of Queen Elizabeth Near Dublin, Ireland

[21] Appl. No.: 27,951

[22] Filed: Mar. 19, 1987

[30] Foreign Application Priority Data

Mar. 24, 1986 [GB] United Kingdom ................ 8607231

[51] Int. Cl.$^4$ ....................... G01N 25/00; G01N 7/16
[52] U.S. Cl. ....................... 374/54; 374/33; 73/19
[58] Field of Search ................ 374/33, 35, 54; 73/19

[56] References Cited

U.S. PATENT DOCUMENTS

| 2,387,878 | 10/1945 | Brown .................... 73/19 |
| 2,414,364 | 1/1947 | Dietrert et al. .......... 374/54 |
| 3,490,266 | 1/1970 | Bennett et al. .......... 73/19 |
| 3,564,901 | 2/1971 | Megrue .................. 374/54 |
| 3,578,404 | 5/1971 | Walles et al. ........... 73/19 |
| 3,589,172 | 6/1971 | Bowman .................. 73/19 |
| 3,593,564 | 7/1971 | Kraus ................... 374/54 |
| 3,659,452 | 5/1972 | Atwood et al. .......... 374/54 |
| 3,681,026 | 8/1972 | Holden .................. 73/19 |
| 3,812,705 | 5/1974 | Boillot ................. 73/19 |
| 4,072,050 | 2/1978 | Ter-Minassian .......... 374/33 |
| 4,314,969 | 2/1982 | Arthur et al. .......... 73/19 |

FOREIGN PATENT DOCUMENTS

| 1012667 | 5/1963 | United Kingdom . |
| 1004203 | 3/1964 | United Kingdom . |
| 1244341 | 9/1968 | United Kingdom . |
| 1214850 | 12/1970 | United Kingdom ............... 73/19 |
| 0226200 | 9/1968 | U.S.S.R. ..................... 374/54 |
| 1121611 | 10/1984 | U.S.S.R. ..................... 374/54 |

OTHER PUBLICATIONS

Ryan, D. H. et al., "Thermopiezic analysis: gas absorption and desorption studies on milligram samples", J. Phys. E: Sci. Instrum. 19 (1986), pp. 693–694.

"An Automatic Thermomanometer for Hydrogen Absorption and Desorption Studies on Milligram Samples", Surface and Coatings Technology, 28 (1986), pp. 383–386.

Primary Examiner—William A. Cuchlinski, Jr.
Assistant Examiner—Thomas B. Will
Attorney, Agent, or Firm—Arnold, White & Durkee

[57] ABSTRACT

A method and apparatus for thermal analysis of a solid or liquid sample which evolves or absorbs gas on heating or cooling, wherein the sample is heated or cooled in an enclosed space, the temperature of the sample and the pressure of the gas are continuously monitored by temperature and pressure sensors respectively, and measurements of sample temperature and gas pressure are input to a data processor which also controls the temperature change of the sample. The value of gas pressure as a function of sample temperature and the rate of change of this value with respect to sample temperature are calculated; these functions are characteristic of the sample or of a component of the sample under analysis.

14 Claims, 4 Drawing Sheets

THERMAL ANALYSIS

BACKGROUND OF THE INVENTION (1) Field of the Invention

The present invention relates to a method of thermal analysis of solids and liquids hereinafter called thermopiezic analysis (TPA) and to an apparatus for carrying out the same method.

(2) Description of the Prior Art

There are several methods of thermal analysis of solids or liquids which are in widespread use and these include thermogravimetric analysis (TG), differential thermal analysis (DTA) and differential scanning calorimetry (DSC). Many solids (for example, carbonates, sulphates, hydrated salts, silicate minerals, organic solids and hydrogenated metals) when heated will decompose and evolve gases at a characteristic temperature or temperatures. Other solids will react with ambient gas to form compounds (for example, certain metals react with hydrogen to form hydrides). The weight change as a result of these reactions is continuously monitored at a constant heating rate in thermogravimetric analysis. Differential thermal analysis is a technique based on continuously monitoring the temperature of a sample and of a reference which are being heated and recording the temperature difference between the two as a function of temperature. In differential scanning calorimetry the difference in power which must be applied to make a sample and a reference follow a desired heating rate is monitored.

BRIEF SUMMARY OF THE INVENTION

IT is an object of the present invention to provide a method of thermal analysis which is more sensitive than any of the above known methods and which is also quantitative, that is, it can measure how much of a sample is present or how much of a particular component is present within a sample.

According to the present invention there is provided a method of thermal analysis of a solid or liquid sample which evolves or absorbs gas on heating or cooling, which comprises locating the sample in a portion of a closed volume, heating and/or cooling the sample in a controlled manner, and monitoring the pressure of gas in the closed volume. Normally the value of gas pressure as a function of sample temperature and the rate of change of this value with respect to sample temperature are calculated; these functions are characteristic of the sample or of a component of the sample under analysis. Preferably the gas pressure is monitored continuously. Preferably the portion of the closed volume which is heated is relatively small compared to the total of the closed volume, or the effect of heating is confined to the sample and (if necessary) a small portion of the closed volume around it.

Preferably the total closed volume is at least ten times greater than the said portion of the closed volume which is heated. This ensures that the volume of gas being heated within the small portion of the closed volume containing the sample is small relative to the total volume of gas in the closed volume and therefore the pressure change associated with the sample is not unduly influenced by the pressure change of the heated gas, since the volume of hot gas is as small as possible.

If P is the pressure of gas in the closed volume containing the sample and T is the sample temperature, then the functions $P(T)$ and $dP(T)/dT$ are characteristic of both the mass and nature of the sample or the components of the sample under analysis.

The present invention also relates to a thermal analyser for carrying out the method of the invention comprising a container means for holding the sample to be analysed, a heating means for varying the temperature of the sample within the container means, a temperature sensor for detecting the temperature of the sample, a chamber connectable with the container means, and a pressure sensor which detects the gas pressure within the chamber, the chamber having a substantially greater volume than the container means.

The analyser may be provided with a pump for evacuating the chamber and the container means, and a gas tank for supplying gas to the container means and chamber.

Preferably the container means takes the form of a sample tube which has a volume at least 10 times smaller than the chamber. This ensures that the pressure change associated with the sample is not unduly influenced by the pressure change of the heated gas.

In practice the expansion due to heating of the gas leads to some of the pressure increase of the order of 4%. This background effect can be reduced by increasing the total volume of the chamber, even up to 100 times the volume of the sample tube, but with a consequent loss of sensitivity. If only a small sample is available and/or sensitivity is important, the volume of the chamber can be reduced to 5 times the volume of the sample tube, but it is necessary to correct for the background pressure increase due to expansion and it is also necessary to keep the pressure sensors away from the high temperature of the sample tube.

The analyser may also be provided with data processing means, e.g. a microcomputer, which receives inputs from the temperature sensor and the pressure sensor. The data processing means may also control the supply of current to the heating means so that the temperature of the sample is raised at a certain preset rate which normally is a constant rate. The power supply to the pressure sensor may also be provided by the data processor. A mass spectrometer may be attached to identify evolved gases.

The analyser of the invention may suitably be operated over a temperature range from room temperature to 1000° C. (or even higher, depending upon the ability of the heating means and the sample container to withstand high temperatures) and a pressure range from vacuum to 2 bar. A suitable heating rate may be chosen from 1° C. to 50° C. per minute.

BRIEF DESCRIPTION OF THE SEVERAL VIEWS OF THE DRAWINGS

One embodiment of a method and analyser in accordance with the present invention will now be described with reference to the accompanying drawings, wherein.

DETAILED DESCRIPTION

Figure 1:
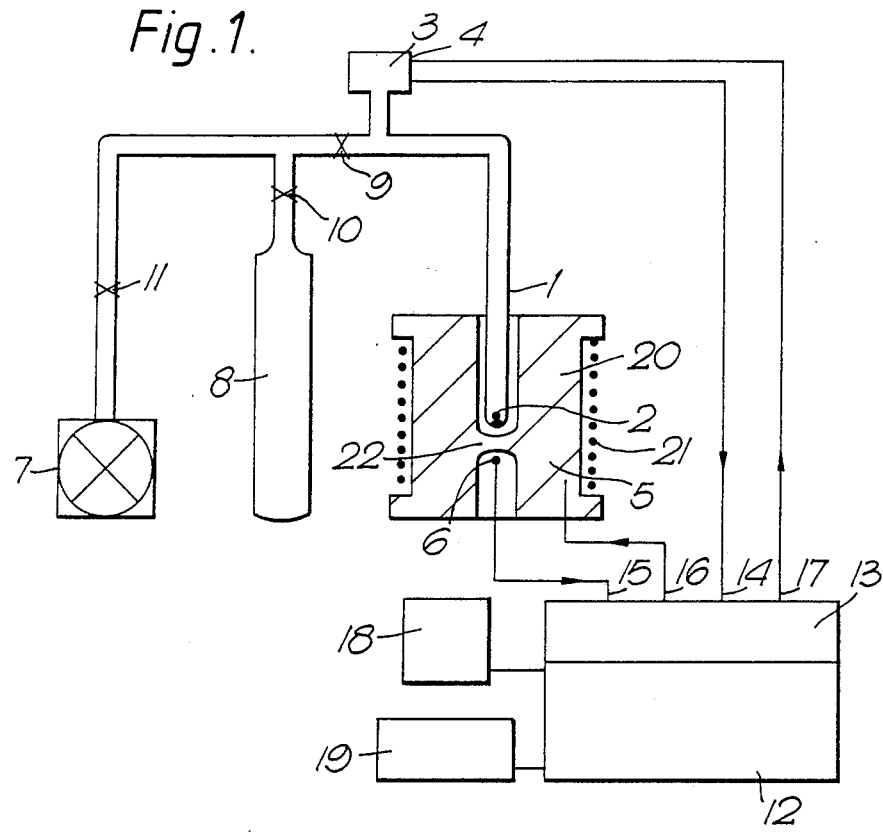
FIG. 1 is a schematic representation of the thermopiezic analyser of the invention (not drawn to scale)

As shown in FIG. 1 the analyser comprises a small-bore quartz tube 1 in which a sample 2 to be analysed may be enclosed. The sample tube 1 is connected to a chamber 3 in which the pressure is continuously measured by means of a pressure sensor 4. The temperature of the sample 2 within the sample tube 1 is varied by means of a furnace 5 which comprises a bobbin-shaped block 20 of metal, suitably the nickel based alloy sold under the Trade Mark INCONEL, heated by an electric current through a coil of wire 21 wound around the block. The wire is suitably of the kind sold under the Trade name KANTHAL. The part of the sample tube outside the furnace is surrounded by insulating material (not shown) so that substantially the whole of the sample tube is heated. The temperature of the sample 2 is monitored by a temperature sensor 6. A bridge 22 across the hollow core of the block 20 separates the sample tube 1 from the temperature sensor 6. The sample tube 1 and the chamber 3 may be evacuated by means of a pump 7, and refilled with gas from a gas supply tank 8. The analyser is provided with three valves 9, 10 and 11 for use in evacuating the sample tube 1 and chamber 3 and refilling them with gas.

The analyser is controlled by a microcomputer 12 via an interface 13. The microcomputer 12 receives a voltage input 14 from the pressure sensor 4 and a voltage input 15 from the temperature sensor 6. The microcomputer 12 also controls a current output 16 to the furnace 5 and provides a current output 17 to the pressure sensor 4. A monitor 18 is provided for displaying during analysis the pressure read by the pressure sensor 4 as a function of temperature and data stored by the microcomputer 12 may be presented graphically on a printer/plotter 19 as P(T) or as its derivative dP(T)/dT, as shown in FIGS. 2–5. The microcomputer may also correct for the percentage of the pressure increase which is due to expansion of the gas as a result of heating.

In a particular embodiment of the thermopiezic analyser the sample tube 1 is 40 mm long and has an internal diameter of 2 mm while the chamber 3 has a volume of 2 cm$^3$. A typical sample mass is in the range 1 to 10 mg.

In use, the sample 2 to be analysed is placed in the sample tube 1. The sample tube 1 and the chamber 3 may then be evacuated by pump 7 and refilled with gas from the gas supply tank 8, if desired. Before analysis of the sample 2 begins, the valve 9 is closed. The sample 2 is then heated by means of the furnace 5, the current supply 16 to which is controlled by the microcomputer 12 in such a way that the temperature read at the temperature sensor 6 rises at a preset rate R. The microcomputer 12 also supplies a current output 17 to the pressure sensor 4 and receives an input 14 from the pressure sensor 4 and an input 15 from the temperature sensor 6. Pressure read by the pressure sensor 4 is displayed as a function of temperature on the monitor 18 and the printer/plotter 19 displays P(T) or dP(T)/dT graphically.

The performance achieved by the analyser described above may be summarised as follows:

Temperature range: Room temperature to 1000° C.
Pressure range: Vacuum to 2 bar.
Heating range: 1° C. to 50° C. per minute.
Heating control error: less than 1° C.
Sample lag+: less than 4° C.
Resolution$^x$: $10^{-8}$ moles = 20 ng of $H_2$.

+Sample lag is the difference between the heating block temperature and the actual sample temperature.

×Resolution is a measure of the smallest pressure change detectable, expressed as a quantity of gas.

The method of thermopiezic analysis and the analyser of this invention have a wide range of uses which include, but are not limited to, quantitative analysis of gas-evolving phases, measurement of hydrogen content of metals and alloys by heating to a sufficiently high temperature to expel the hydrogen, measurement of moisture content, identification of the phases present in unknown mixtures, soil analysis and the study of gas-solid reactions including hydrogen uptake in metals.

FIG. 2(a) shows a graph of pressure against temperature obtained in analysis of $Nd_2Fe_{14}B$ by the method of the invention, with the closed volume of the analyser being filled with hydrogen at 1.4 bar. A 50 mg sample of $Nd_2Fe_{14}B$ was heated at a constant rate of temperature increase of 25° C. per minute. The results show that at about 300° C. the hydrogen pressure drops rapidly, due to the hydrogen reacting with the alloy to form a hydride. Examination has shown that the alloy crystallography has remained essentially unchanged and the properties of the alloy have been modified but not altered substantially.

As heating is continued to temperatures between 350° C. and 700° C., the hydrogen is released again. At about 750° C., the hydrogen reacts again but examination has shown that at this temperature the alloy has segregated, the hydride of neodymium has formed, while the iron and boron form other alloys. Continued heating up to 1000° C. causes the hydrogen to be given off again.

This type of analysis allows one to identify and select optimum conditions for hydrogenation of the alloy in question, with a view to preparing an alloy with improved Curie temperature and magnetisation properties, for use in the manufacture of magnets. Similar analyses can be carried out on other rare earth metal alloys.

In the manufacture of magnets, it is usual to pulverise a lump of alloy and then sinter the powder. Hydrogen can be used to achieve pulverisation in a much more economical manner than physical grinding. The thermopiezic analysis of the invention enables one to identify the optimum conditions for this pulverisation treatment. In addition, the alloy hydride has better properties than the untreated alloy.

FIG. 2(b) likewise shows a plot of pressure against temperature resulting from the analysis of $Y_{60}Fe_{40}H_{150}$ in vacuo. The solid line is P vs. T, the dotted line is dP/dT vs. T.

$Y_{60}Fe_{40}H_{150}$ is an amorphous alloy into which hydrogen has been introduced by electrolysis. The sample is heated in vacuum so that the analysis is not influenced by any hydrogen remaining in the system. The derivative curve shows one peak for the release of hydrogen but with an interruption due to the sample crystallising.

This analysis enables one to measure the quantity of hydrogen in the alloy (it was by this method that the formula $Y_{60}Fe_{40}H_{150}$ was determined); it enables one to identify the temperature range in which the release of hydrogen occurs; and it facilitates the study of the release of hydrogen before and after crystallisation.

Amorphous alloys of this kind are candidates for hydrogen storage materials and it is therefore useful to analyse the way in which hydrogen is absorbed and released by the alloy.

Figure 3:
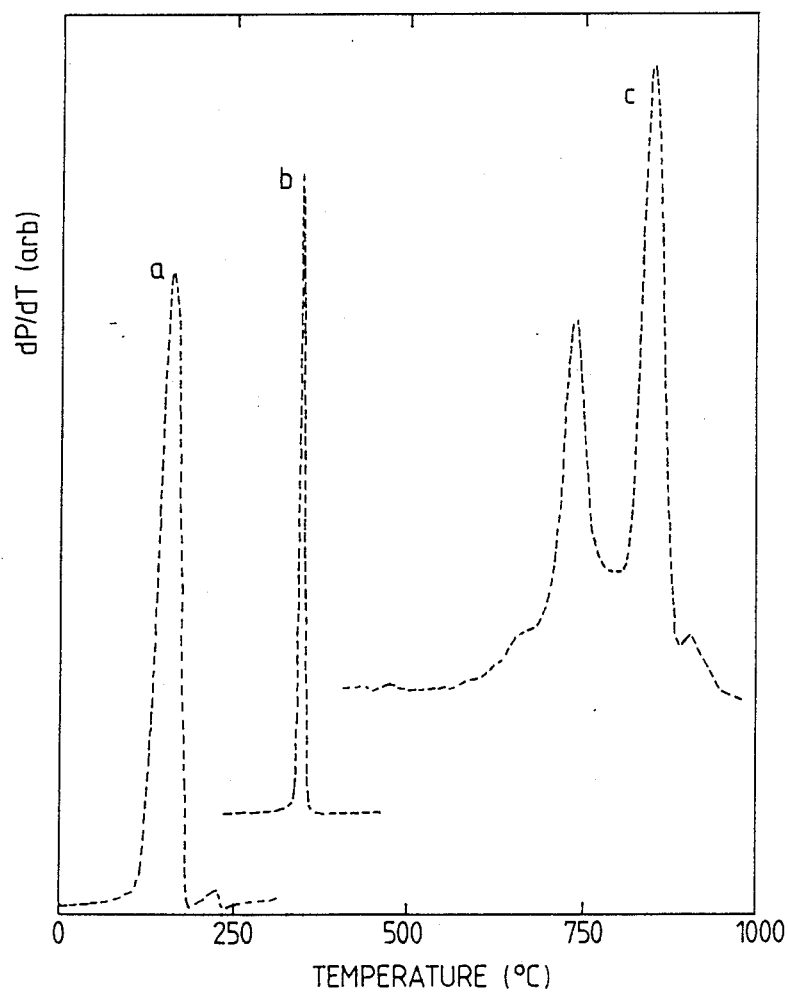
FIG. 3 shows three further examples of graphic outputs $dP/dT$ in arbitrary units versus T for examples (a) $NaHCO_3$ (b) $KIO_4$ and (c) Hectorite heated in vacuo.

FIG. 3 shows graphic outputs dP/dT in arbitrary units versus T for examples (a) $NaHCO_3$, (b) $KiO_4$ and (c) Hectorite, heated in vacuo.

Figure 4:
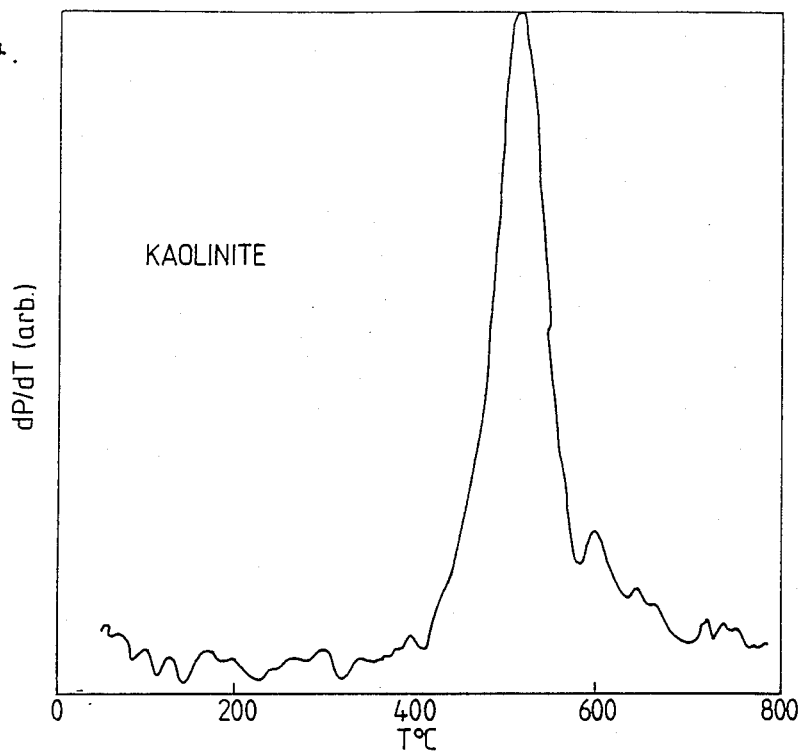
FIGS. 4 and 5 are comparative graphic outputs for a simple Kaolinite mineral (FIG. 4) and a mixed layer Kaolinite/Smectite mineral, run under identical conditions.

FIG. 4 shows the derivative curve dP(T)/dT for analysis of Kaolinite, which releases water on heating. The pressure is kept low, of the order of 100 millibars, in order to avoid condensation of the water vapour, and a very small sample of the clay is analysed, using very sensitive transducers to measure the pressure.

Figure 5:
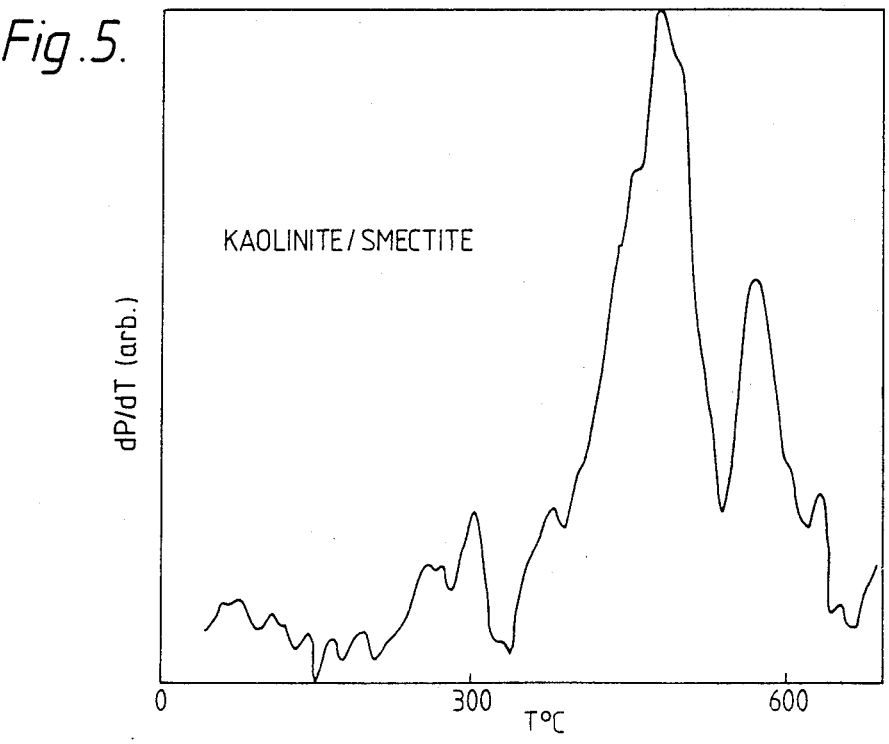

FIG. 5 shows a comparable analysis for a mixed layer Kaolinite/Smectite mineral run under identical conditions. It will be observed that the dehydroxylation peaks are different, one of the peaks being characteristic of the smectite component of the mixture. These clays are of interest for catalytic purposes.

Figure 6:
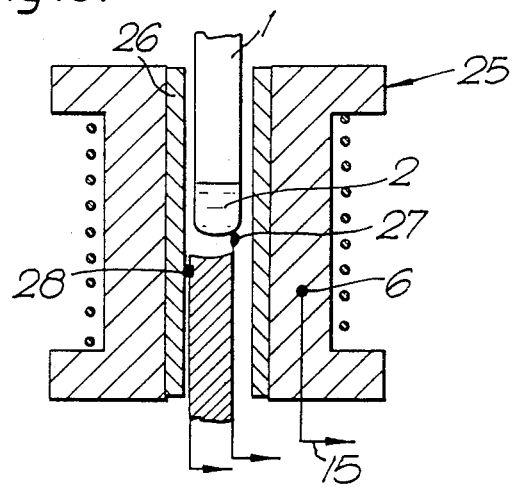
FIG. 6 is a diagram of an alternative embodiment of a heating unit which enables differential thermal analysis to be carried out at the same time as thermopiezic analysis.
Figure 2:
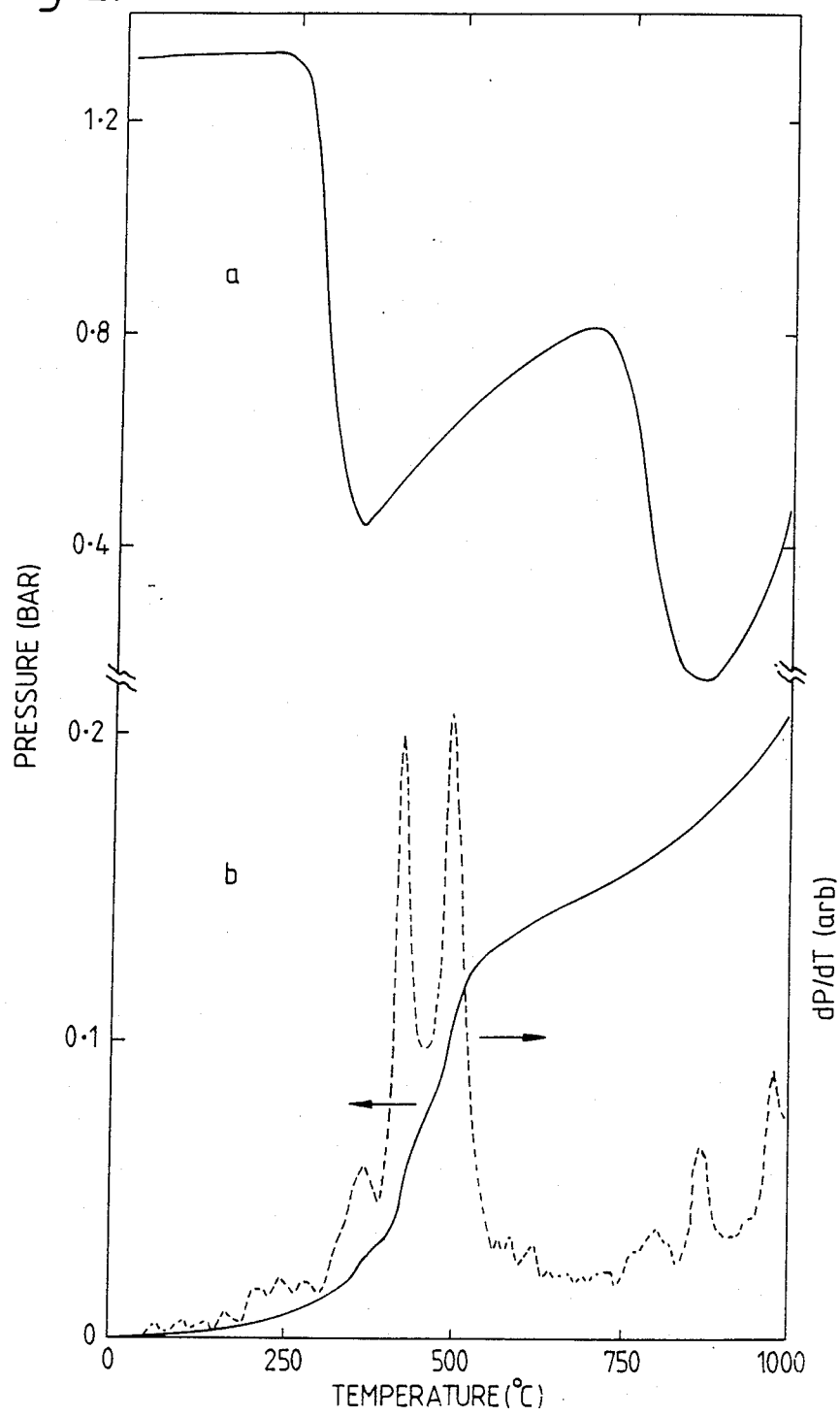
FIG. 2(a) is an example of a graphic output from the thermopiezic analyser of the invention, showing results of an analysis of $Nd_2Fe_{14}B$ in 1.4 bar of hydrogen.
FIG. 2(b) is a further example of a graphic output, showing results of an analysis of $Y_{60}Fe_{40}H_{150}$ in vacuo.

FIG. 6 shows an alternative heating and temperature sensor assembly which can be used for determining differential thermal analysis (DTA) at the same time as thermopiezic analysis. The furnace 25 is lined with an annular layer of refractory material 26, to even out the temperature distribution. One temperature sensor 27 is in contact with the sample tube 1, inside the hollow core of the furnace. A second temperature sensor 28 is mounted a short distance away, preferably on the surface of the refractory material 26. The space between the sensors 27 and 28 is filled with refractory material for support purposes. A third temperature sensor is mounted inside the furnace block to monitor the heating of the furnace.

The difference in temperature between the first and second sensors 27 and 28 is continuously monitored. If the temperature of the sample in tube 1 changes as a result of a reaction occurring in the sample, for example if crystallisation or hydrogen absorption releases heat, or if release of water absorbs heat, then the temperature of the sample will vary relative to the temperature of the furnace. This differential thermal analysis enables one to study the heat of reaction at the same time as carrying out thermopiezic analysis in gas-evolving or gas-absorbing reactions and provides data which can be related to the DTA results of other workers. It also enables the analyser to be used for supplementary study on reactions which do not evolve or absorb gas.

We claim:

1. A method of thermal analysis of a solid or liquid sample which evolves or absorbs gas on heating or cooling, which comprises locating the sample in a portion of a closed volume, heating and/or cooling the sample, continuously monitoring both the temperature of the sample and the pressure of gas in the closed volume, inputting measurements of sample temperature and gas pressure to a data processor, controlling the temperature change of the sample by an output from the data processor, and using the data processor to monitor the value of gas pressure P as a function of sample temperature T.

2. A method according to claim 1 wherein the rate of change dP(T)/dT with respect to sample temperature of the value of gas pressure as a function of sample temperature is calculated.

3. A method according to claim 1 wherein the portion of the closed volume which is heated is relatively small compared to the total of the closed volume.

4. A method according to claim 1 wherein the effect of heating is confined to the sample.

5. The method of claim 4, wherein the effect of heating is further confined to a portion of the closed volume around the sample.

6. A method according to claim 1 wherein the total closed volume is at least ten times greater than the portion of the closed volume which is heated.

7. A method according to claim 1 wherein the sample is heated or cooled at a substantially constant rate.

8. A method according to claim 1, wherein the sample mass is in the range from 1 to 50 mg.

9. A process of testing a solid or liquid material with regard to its performance in evolving or absorbing gas on heating or cooling, which comprises locating a sample of the material in a portion of an enclosed space, heating and/or cooling the sample, continuously monitoring both the temperature of the sample and the pressure of gas in the enclosed space, inputting measurements of sample temperature and gas pressure to a data processor, controlling the temperature change of the sample by an output from the data processor, and using the data processor to monitor the value of gas pressure P as a function of sample temperature T.

10. A thermal analyser for analysing a solid or liquid sample which evolves or absorbs gas on heating or cooling, comprising:
   a container means for holding the sample to be analysed;
   a heating means for varying the temperature of the sample within the container means;
   a temperature sensor for monitoring the temperature of the sample;
   a chamber connectable with the container means, the chamber having a substantially greater volume than the container means;
   a pressure sensor for monitoring gas pressure within the chamber; and
   data processing means connected to receive continuous inputs from the temperature sensor and the pressure sensor, for controlling the heating means, and for monitoring the value of gas pressure P as a function of sample temperature T and the rate of change dP(T)/dT of said value with respect to temperature.

11. An analyser according to claim 10 which is provided with a pump for evacuating the chamber and the container means, and a gas tank for supplying gas to the container means and chamber.

12. An analyser according to claim 10 wherein the container means takes the form of a sample tube which has a volume at least 10 times smaller than the chamber.

13. An analyser according to claim 10 wherein a mass spectrometer is attached to identify evolved gases.

14. An analyser according to claim 10; wherein the container means is adapted to hold a sample of from 1 to 50 mg mass.

* * * * *